US005467651A

United States Patent [19]
Manaka

[11] Patent Number: 5,467,651
[45] Date of Patent: Nov. 21, 1995

[54] DRIVE CONTROL APPARATUS FOR MICROSENSOR

[75] Inventor: Junji Manaka, Tokyo, Japan

[73] Assignee: Ricoh Seiki Company, Ltd., Tokyo, Japan

[21] Appl. No.: 139,695

[22] Filed: Oct. 22, 1993

[30] Foreign Application Priority Data

Oct. 23, 1992 [JP] Japan .................... 4-309405

[51] Int. Cl.$^6$ .................................. G01N 37/00
[52] U.S. Cl. ............................ 73/23.21; 73/25.04
[58] Field of Search ................ 73/25.04, 23.21, 73/1 G, 1 R, 708, 866.1

[56] References Cited

U.S. PATENT DOCUMENTS

| | | | |
|---|---|---|---|
| 4,123,934 | 11/1978 | Höht | 73/25.04 |
| 4,730,479 | 3/1988 | Pyke et al. | 73/23.21 |
| 5,003,812 | 4/1991 | Yagawara et al. | 73/31.06 |
| 5,062,065 | 10/1991 | Lampe | 73/23.21 |
| 5,361,184 | 11/1994 | El-Sharkawi et al. | 361/93 |

FOREIGN PATENT DOCUMENTS

| | | | |
|---|---|---|---|
| 3607065A1 | 9/1986 | Germany . | |
| 0172048 | 8/1986 | Japan | 73/23.21 |

OTHER PUBLICATIONS

Patent Abstracts of Japan No. 1 259 406.
Patent Abstracts of Japan No. 61 217 217.
Patent Abstracts of Japan No. 4 126 937.
Patent Abstracts of Japan No. 59 173 742.
Patent Abstracts of Japan No. 62 187 241.
Patent Abstracts of Japan No. 58 147 770.
Patent Abstracts of Japan No. 56 070 449.

*Primary Examiner*—Richard E. Chilcot, Jr.
*Assistant Examiner*—Max H. Noori
*Attorney, Agent, or Firm*—Lowe, Price, LeBlanc & Becker

[57] ABSTRACT

In the drive control apparatus for microsensor according to the present invention, power is constantly supplied to the microsensor. Also the peripheral humidity is detected, and control is switched between pulse drive control and constantly energized drive control according to the detected value. Also the pulse drive voltage is always supplied in an energized state.

7 Claims, 6 Drawing Sheets

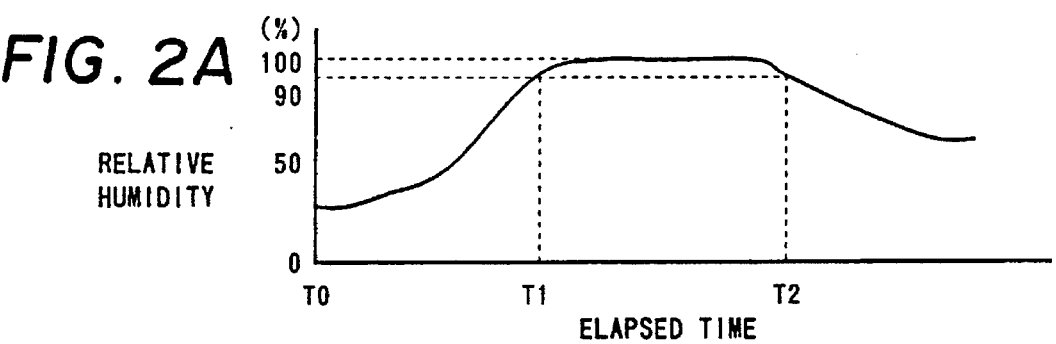
FIG. 2A
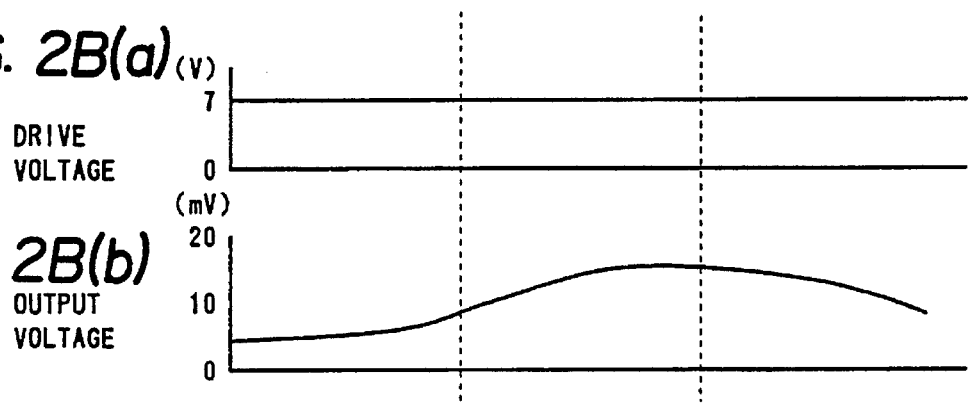
FIG. 2B(a)
FIG. 2B(b)
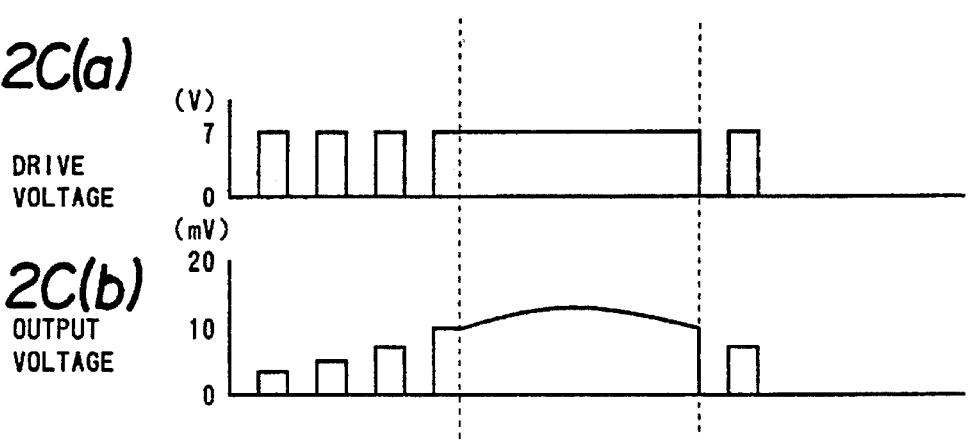
FIG. 2C(a)
FIG. 2C(b)
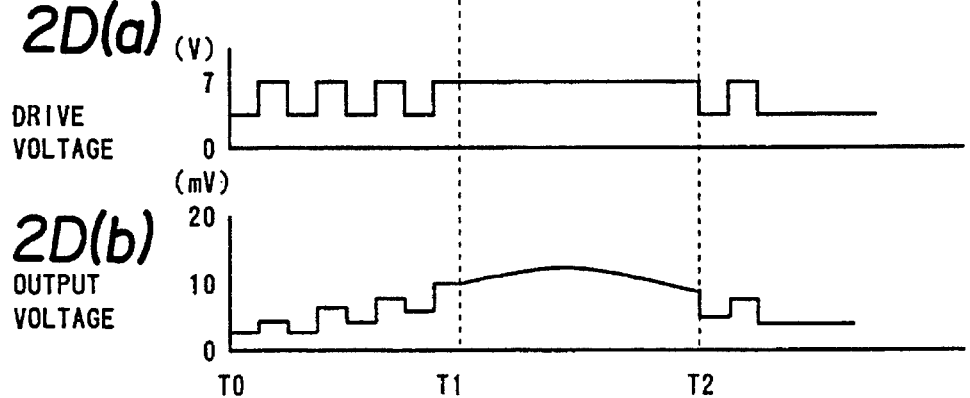
FIG. 2D(a)
FIG. 2D(b)

FIG. 7A
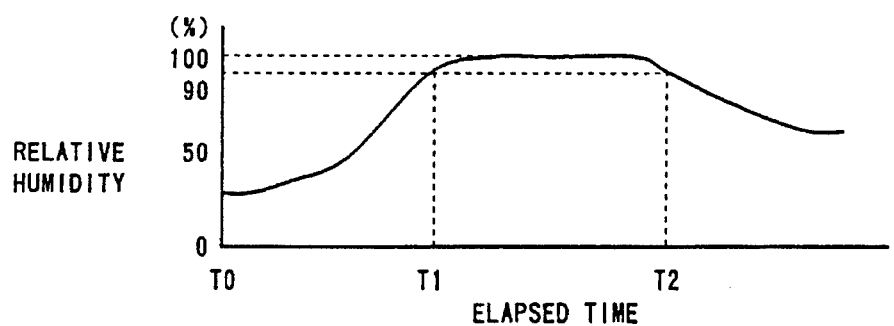
FIG. 7B(a)
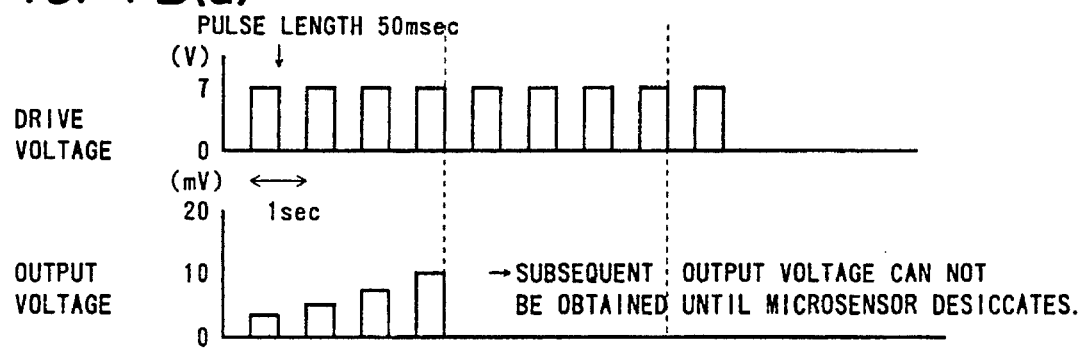
FIG. 7B(b)

5,467,651

DRIVE CONTROL APPARATUS FOR MICROSENSOR

FIELD THE INVENTION

The present invention relates to a drive control apparatus for a microsensor to detect temperature, and more particularly to a drive control apparatus for a microsensor which can prevent dew condensation between electrodes and is available in a wider detection range by eliminating effects by working environment.

BACKGROUND OF THE INVENTION

Description is made hereinafter for an example of a conventional type of microsensor with reference to a temperature sensor making use of changes in thermal conduction. This temperature sensor makes use of a fact that thermal conductivity of a atmospheric gas changes according to a density of vapor (humidity). In the temperature sensor, two thin film resistor heat generating chips each having the same characteristics are used, and one of the chips is sealed with a particular atmosphere such as air having a certain degree of humidity and used as a chip for temperature compensation, while the other chip is located in a space where the atmosphere can circulated to and from the outside and is used as a chip for detection.

With the configuration as described above, the chip for temperature detection is located in the atmosphere having the atmospheric thermal conduction characteristics corresponding to a humidity which is equal to that of the external air, and when a certain quantity of heat is generated in the chip for temperature detection, the temperature goes up to a certain level where the temperature is balanced with a heat capacity corresponding to the thermal conductivity of the space in which the chip for temperature detection is installed. For this reason, the chip for detection enters a state, according to the temperature coefficient, in which the chip has a resistance value corresponding to a temperature in the space. If a heat value of the chip for temperature compensation is kept at the level as that of the chip for temperature detection in this state, a temperature difference corresponding to a difference of absolute humidity in the spaces where the two chips are installed respectively, accordingly a difference between resistance values of the two chips is generated, and an absolute temperature of the external air can be measured by providing the difference between the resistance values as an output indicating imbalance in a bridge circuit.

In this film resistor heat generating chip, temperature changes according to change of a temperature of external air, but in that case also the same temperature change occurs in both the chip for temperature compensation and the chip for temperature detection, so that as a principle output from the bridge circuit described above does not change, and it is possible to detect only the absolute temperature irrespective of the external air temperature.

In a case where characteristics of the sensor is affected by temperature of the working environment for use of the sensor, it is necessary to subtract fluctuation depending on temperature change from the measured temperature using a principle of comparing output data from the temperature compensating section to that from the temperature detecting section. If the temperature compensating section and the temperature detecting section are very close to each other, it is possible to accurately detect a temperature around the detecting section. For this reason, the temperature compensating section and the temperature detecting section should be located at positions close to each other on the same substrate.

FIG. 3 is a cross sectional view illustrating an example of a sensor chip 300 having the configuration as described above, and in this figure, designated at the reference numeral 301 a substrate, at 302 an insulating protective film mounted on the substrate 301, at 303 a heat generating section located on the insulation protective film 302, at 304 a temperature compensating section, at 305 a humidity detecting section, at 306 a air hole provided in the temperature detecting section 305, and at 307 an electrode connected to the heat generating section 303.

FIG. 4 and FIG. 5 are drawings each illustrating a state where the sensor chip 300 having the configuration as show in FIG. 3 has been assembled in a casing, and in the figures, at the reference numeral 401 is designated at a base section, at 402 a lead pin, at 403 a nickel cap which is engaged with the base section 401, at 404 a stainless duplex mesh, at 405 a bonding wire used for connection between the sensor chip 300 and the lead pin 402, at 406 die bond adhesive used to make the sensor chip 300 adhere to the base section 401.

In the configuration described above, generally the sensor chip 300 shown in FIG. 3 has been assembled in a casing and a microsensor has been driven by providing pulse drive control in an energized state with 50 msec pulse width via a power supply unit 601 from the Wheatstone bridge circuit shown in FIG. 6.

In the conventional type of microsensor as described above, however, the sensor is intermittently controlled according to pulse drive, so that in some operating environments the electrode section is sometimes shortcircuited due to dew condensation, as a result output voltage is not obtained, and the functions as a sensor is lost.

Description is made hereinafter for the above-described problem with reference to the related drawings. The state where the peripheral environmental conditions detected by the microsensor are as shown by the graph in FIG. 7 (relative humidity/elapsed time) is assumed. A microsensor has a minute construction and its heat capacity is very small, so that the microsensor is used under the conditions, for instance, that 7 V power is loaded for 1 sec at a pulse rate of once for 50 msec, but when the elapsed time passes over T1, the humidity raises to more than 90% and the subsequent output voltage can not be obtained. This phenomenon occurs because the electrodes are electrically shortcircuited due to dew condensation generated between the electrodes shown in FIG. 3.

SUMMARY OF THE INVENTION

It is an object of the present invention to prevent the electrical shortcircuitry generated due to dew condensation and insure functions of a sensor obtaining output voltage under any operating conditions.

In order to achieve the object as described above, the present invention provides a drive control apparatus for a microsensor, in which a plurality of cavity sections are provided on an airtight substrate at positions facing to each other when stacked, the substrates are stacked via a junction area, thin film heat generating bodies, one for temperature detection and the other for temperature compensation are provided in a bridging form in each space formed by the cavity sections described above; having detecting means for detecting peripheral humidity and control means for selecting pulse drive control (This terms hereinafter defined as pulse drive control in an energized state) or constantly energized drive control depending on a value detected by the aforesaid detecting means.

It is desired that the pulse voltage used for pulse drive control is provided in an energized state.

Also it is desired that the control means switches pulse drive control to constantly energized drive control when a humidity of not less than 90% is detected by the detecting means and constantly energized drive control to pulse drive control mode when the humidity of less than 90% is detected by the detecting means.

In the drive control apparatus for a microsensor according to the present invention, power is constantly supplied to the microsensor. Also the peripheral humidity is detected, and control is switched between pulse drive control and constantly energized drive control according to the detected value. Also the pulse drive voltage is always supplied in an energized state. Also the pulse drive control mode is switched to the constantly energized drive control mode when a humidity of not less than 90% is detected and the constantly energized drive control is switched to pulse drive control when a humidity of less than 90% is detected.

Other objects and features of this invention will become understood from the following description with reference to the accompanying drawings.

BRIEF DESCRIPTION OF THE DRAWINGS

FIGS. 2A–2D are graphs showing a control operation of the drive control apparatus for a microsensor shown in FIG. 1;

FIGS. 7A–7B are graphs showing problems relating to pulse drive control in a conventional type of microsensor.

DESCRIPTION OF THE EMBODIMENT

Figure 1:
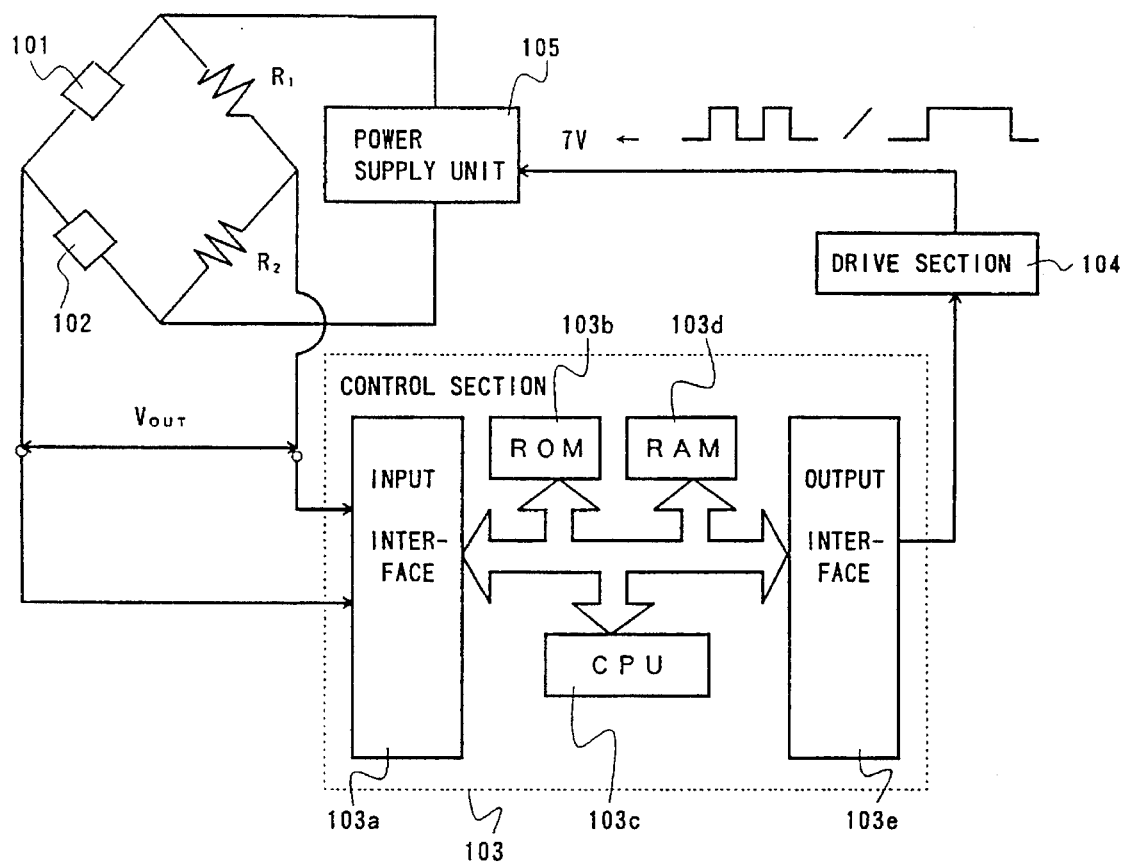
FIG. 1 is a drawing illustrating general configuration of a drive control apparatus for a microsensor according to the present invention.
Figure 3:
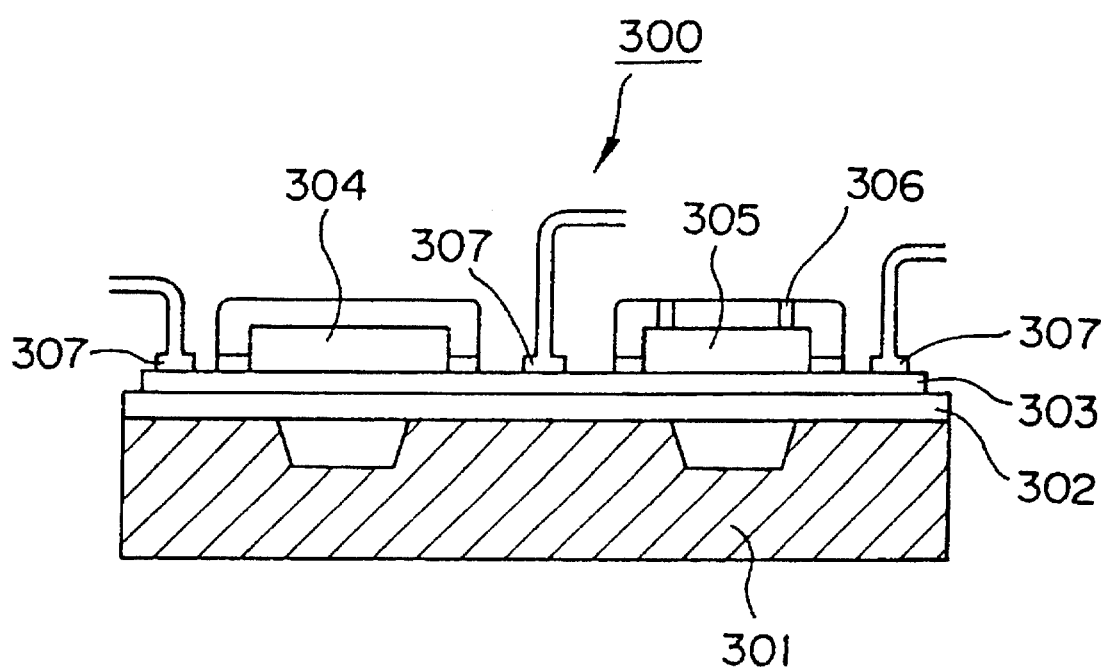
FIG. 3 is a cross sectional view illustrating configuration of a sensor chip.

Description is made hereinafter for an embodiment of the present invention with reference to the attached drawings. FIG. 1 is a drawing illustrating general configuration of a drive control apparatus for a microsensor according to the present invention. In this figure, at the reference numeral 101 is designated a humidity detecting section, at 102 a temperature compensating section, at 103 a control section, at 103a an input interface which receives a signal from the sensor and sends the input signal to a data bus, at 103b a ROM in which programs to execute various types of control processing are stored, at 103c a CPU to execute various types of processing according to the programs stored in the ROM 103b, at 103d a RAM to store results or data processed by the CPU 103c, and at 103e an output interface to output control instructions according to specified formats. Also at the reference numeral 104 is designated a drive section which selectively drives a power supply unit 105 under a pulse drive control or a constantly energized drive control, and at 105 a power supply unit.

Figure 4:
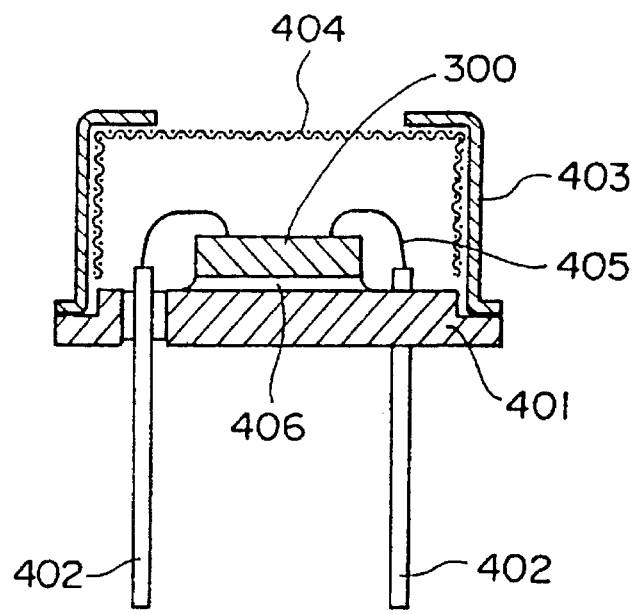
FIG. 4 is a cross sectional view illustrating a state where the sensor chip shown in FIG. 3 has been assembled in a casing.
Figure 5:
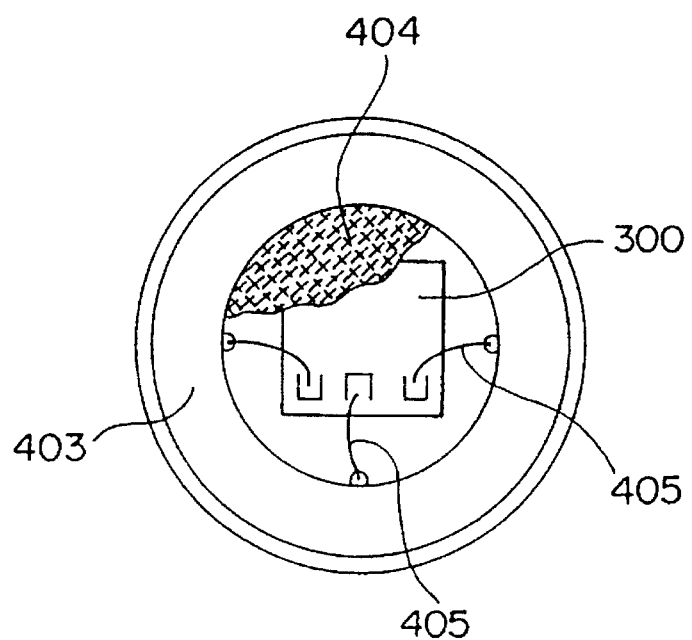
FIG. 5 is a top view of the state where the sensor chip shown in FIG. 3 has been assembled in a casing.
Figure 6:
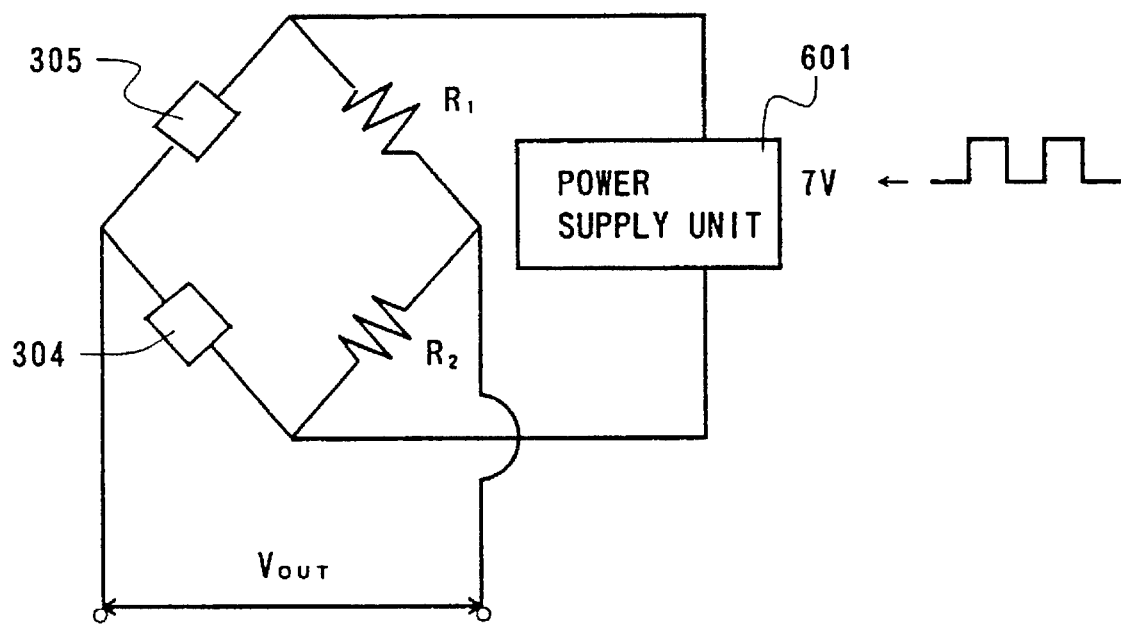
FIG. 6 is a circuit diagram shown a Wheatstone bridge circuit to drive a microsensor.

Now description is made for the operations in the configuration as described above with reference to FIG. 2. FIG. 2A illustrates a graph which shows a relationship between relative humidity and elapsed time. In FIG. 2B, pulse drive is stopped without any specific control being executed, and 7 V is constantly loaded from the power supply unit 105. As a result, the temperature goes up in the entire casing shown in FIG. 4 and FIG. 5. For instance, when the peripheral temperature is 20° C., the temperature in the casing is 38° C. For this reason, even when the temperature is 20° C. and the humidity is 90%, as the peripheral temperature around the casing is high, the humidity drops to a range from less than 90% to 60%. Accordingly, dew condensation does not occur in the sensor chip or the casing, nor occurs electric shortcircuitry.

In FIG. 2C, pulse drive control is switched to constantly energized drive control when a humidity is not less than 90%, and the state is maintained until the humidity drops to less than 90%. Namely, the sensor always makes determination as to whether a humidity has raised to 90% or not, If the sensor determines that the humidity has raised up to 90%, the control section issues a control signal to the drive section 104, and the drive section 104 switches the power supply unit from pulse drive control mode to constantly energized drive control mode. On the contrary if the control section 103 determines depending on a signal from the sensor chip that the humidity has dropped to less than 90%, the control 103 issues a control signal to the drive section 104, and the drive section 104 switches the power supply unit 105 from constantly energized drive control mode to pulse drive control mode.

In FIG. 2D, during the pulse drive control shown in FIG. 2C, pulse drive control is executed under a pulse voltage in a range from 4 V to 7 V without giving any pause to the voltage, and when the control section 103 determines that the humidity has raised up to not less than 90% as shown in FIG. 2C, the drive section 104 witches from pulse drive control under pulse voltage in a range from 4 V to 7 V to constantly energized drive control, and the state is maintained until the humidity drops to less than 90%.

As described above, in the drive control apparatus for a microsensor according to the present invention, the microsensor is constantly energized, peripheral humidity is detected, and switching between pulse drive control and constantly energized drive control is executed according to a detected value, a pulse voltage in pulse drive control is provided in an energized state, pulse drive control is switched to constantly energized drive control when the humidity of not less than 90% is detected, and constantly energized drive control is switched to pulse drive control when the humidity of less than 90% is detected, so that electric shortcircuitry due to dew condensation can be prevented, output voltage can be obtained in any operating environment, and functions as a sensor are fully insured.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A drive control apparatus for a microsensor in which a plurality of cavity sections are provided on an airtight substrate at positions facing each other when said substrates are stacked via a junction area, and thin film heat generating bodies for temperature detection and temperature compensation are installed in a bridge form in each of the plurality of spaces each formed by said cavity sections, wherein a predetermined voltage is constantly supplied to the microsensor above a predetermined humidity.

2. A drive control apparatus for a microsensor in which a plurality of cavity sections are provided on an airtight substrate at positions facing to each other when said substrates are stacked via a junction area, and thin film heat generating bodies for temperature detection and temperature compensation are installed in a bridge form in each of the plurality of spaces each formed by said cavity sections, the drive control apparatus comprising:

a detecting means for detecting the peripheral humidity; and a control means for selecting pulse voltage or constant voltage according to the peripheral humidity detected by said detecting means.

3. The drive control apparatus of claim 2 further comprising means for selecting a pulse drive control to apply the pulse voltage to the microsensor or a constantly energized drive to apply the constant voltage to the microsensor in response to said control means.

4. A drive control apparatus for a microsensor according to claim 3, wherein said pulse drive control is in an energized state.

5. A drive control apparatus for a microsensor according to claim 3, wherein a pulse voltage for said pulse drive control is provided in an energized state.

6. A drive control apparatus for a microsensor according to claim 2, wherein said control means switches from a constantly energized drive control when said detecting means detects a humidity of not less than a specific value to a pulse drive control when the detecting means detects a humidity of less than the specific value.

7. A drive control apparatus for a microsensor according to claim 6, wherein said specific value is approximately 90%.

* * * * *